US009738705B2

(12) United States Patent
Ma et al.

(10) Patent No.: US 9,738,705 B2
(45) Date of Patent: Aug. 22, 2017

(54) MONOCLONAL ANTIBODIES SPECIFIC FOR CRY1CA AND RELATED DETECTION METHODS

(71) Applicant: Dow AgroSciences LLC, Indianapolis, IN (US)

(72) Inventors: Eric Hongzheng Ma, Zionsville, IN (US); Guomin Shan, Carmel, IN (US); Todd P. Glancy, Fairmount, IN (US); Sarah E. Canada, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 51 days.

(21) Appl. No.: 14/693,974

(22) Filed: Apr. 23, 2015

(65) Prior Publication Data

US 2015/0309027 A1 Oct. 29, 2015

Related U.S. Application Data

(60) Provisional application No. 61/985,654, filed on Apr. 29, 2014.

(51) Int. Cl.
*C07K 16/12* (2006.01)

(52) U.S. Cl.
CPC ...... *C07K 16/1278* (2013.01); *C07K 2317/14* (2013.01); *C07K 2317/33* (2013.01); *G01N 2333/325* (2013.01); *G01N 2430/10* (2013.01)

(58) Field of Classification Search
None
See application file for complete search history.

(56) References Cited

U.S. PATENT DOCUMENTS

| | | | | |
|---|---|---|---|---|
| 9,284,573 B2 | 3/2016 | Meade et al. | | |
| 2009/0143298 A1* | 6/2009 | Malvar | C07K 14/325 | 514/2.1 |
| 2012/0317681 A1* | 12/2012 | Meade | A01N 63/02 | 800/302 |
| 2013/0025006 A1* | 1/2013 | Meade | C12N 15/8286 | 800/302 |

OTHER PUBLICATIONS

Shan et al., A Highly Specific Enzyme-Linked Immunosorbent Assay for the Detection of Cry1Ac Insecticidal Cristal Protein in Transgenic WideStrike Cotton, J. Agric. Food Chem., 55, (2007), p. 5974-5979.*

International Search Report, PCT/US15/27198, dated Jul. 13, 2015, (6 pages).*

Herrero et al., Mutations in the Bacillus thuringiensis Cry1CA toxin demonstrate the role of domains II and III in specificity towards Spodoptera exigua larvae, Biochem J. (2004) 507-513.

Valicente et al., Transformation of Maize Elite Lines with cry1Ca of Bacillus thuringiensis to control Spodoptera frugiperda, 6th Pacific Rim Conference on the Biotechnology of Bacillus thuringiensis and its Environmental Impact, Victoria BC, 2005, 81-83.

Wang et al., Isolation of single chain variable fragment (scFv) specific for Cry1C toxin from human single fold scFv libraries, Toxicon (2012), 1290-1297.

Mang et al., Bio-safety evaluation of Cry1Ac, Cry2Ab, Cry1Ca, Cry1F and Vip3Aa on Harmonia axyridis larvae, Journal of Applied Entomology, Mar. 2016: 1-8.

* cited by examiner

*Primary Examiner* — Ram R Shukla
*Assistant Examiner* — Ellen J Marcsisin
(74) *Attorney, Agent, or Firm* — Ronald S. Maciak

(57) ABSTRACT

Described herein are murine monoclonal antibodies and methods useful for determining and quantitating the presence of Cry1Ca delta endotoxin. The claimed antibodies specifically bind the core toxin region making them suitable for detecting the native full length Cry1Ca toxin as well as the amino core toxin and N-terminal 29 residue truncated forms.

17 Claims, 2 Drawing Sheets

MONOCLONAL ANTIBODIES SPECIFIC FOR CRY1CA AND RELATED DETECTION METHODS

CROSS-REFERENCE TO RELATED APPLICATIONS

This Application claims priority from, and benefit of, U.S. Provisional Application 61/985,654 filed on Apr. 29, 2014. The entire contents of this application are hereby incorporated by reference into this Application.

TECHNICAL FIELD

The present invention is generally in the field of immunology and relates to monoclonal antibodies (mAbs) that specifically bind to insecticidal delta-endotoxins known as Cry1Ca, hybridoma cells producing such antibodies, and enzyme-linked immune-sorbent assays (ELISA) for detecting Cry1Ca proteins in a range of samples.

BACKGROUND OF THE INVENTION

*Bacillus thuringiensis* is a gram positive bacterium that produces a variety of crystalline protein toxins during sporulation generally referred to as delta-endotoxins or Cry proteins. Many of these are highly toxic to a range of agronomic insect pests but are generally harmless to mammals and most other organisms. One such delta-endotoxin, Cry1Ca, is insecticidal to certain lepidopteran pests found in North and South America corn fields.

Cry1Ca has been shown to effectively control fall armyworm, *Spodoptera frugiperda*, and Cry1Fa resistant fall armyworm when expressed in maize plants as a full length protein (Sheets, J., et al., *Entomological Society of America*, Annual Meeting, Nov. 12, 2013, Austin Tex.). The full length Cry1Ca holotoxin is cleaved by native enzymes in the insect gut to produce a core toxin having approximately 624 residues of the amino terminus depending on the insect and gut conditions. Cry1Ca core toxin-containing proteins and genes are therefore attractive candidates for developing recombinant crop plants such as corn, soy, cotton, canola, and others often referred to as genetically modified (GM) plants.

Companies which develop and market GM crop seeds containing recombinant DNA that confer beneficial new traits are required to formulate, implement and adhere to strict product stewardship plans. These stewardship plans require the use of validated quantitative and qualitative protein detection methods for the recombinant protein to track trait introgression and seed production activities, as well as to monitor the GM trait during and after harvest. These detection methods must be facile and robust enough to use under good laboratory practice (GLP) and non-GLP conditions. Moreover the methods must be user friendly enough to be easily employed by farmers in the field, grain dealers at the silo, and customs officials at the borders. Therefore, robust, high quality, user friendly protein detection methods and commercial kits are useful and necessary.

While immunoassays are well-known in the art, developing robust, high quality, validated ELISA methods that are reproducibly able to detect a particular transgenic protein product in an array of plant tissue in both lab and field settings is neither trivial nor routine. Still more challenging is to find antibody pairs that are particularly well suited to the development of a lateral flow strip ELISA for detecting Cry1Ca expressed by a transgenic event in a crop.

SUMMARY OF THE INVENTION

The present invention provides a panel of monoclonal antibodies (Table 1) and the hybridoma cell lines that produce them. The table below lists the hybridoma line designations and their corresponding ATCC deposit designations that were deposited with the American Type Culture Collection in accordance with the terms of the Budapest Treaty. The invention includes a method for identifying the presence of an Cry1Ca enzyme comprising: a) immobilizing a first monoclonal antibody of Claim 1 onto an assay surface then washing said assay surface; b) contacting said assay surface with a liquid suspected of containing Cry1Ca for a period of time sufficient to allow binding then washing said assay surface; c) contacting said assay surface with a different second antibody of the invention conjugated to a reporting group for a period of time sufficient to allow binding of said second conjugated monoclonal antibody then washing said assay surface; and, d) detecting the presence or absence of said reporting group.

The invention also includes methods of using the claimed mAbs for isolating or detecting Cry1Ca comprising: a) immobilizing said antibody onto a surface; b) contacting said immobilized antibody with a mixture containing Cry1Ca; c) separating said immobilized antibody bound to Cry1Ca from said mixture; and d) recovering Cry1Ca by removing the antibody-bound Cry1Ca from said immobilized antibody.

DETAILED DESCRIPTION

Figure 1:
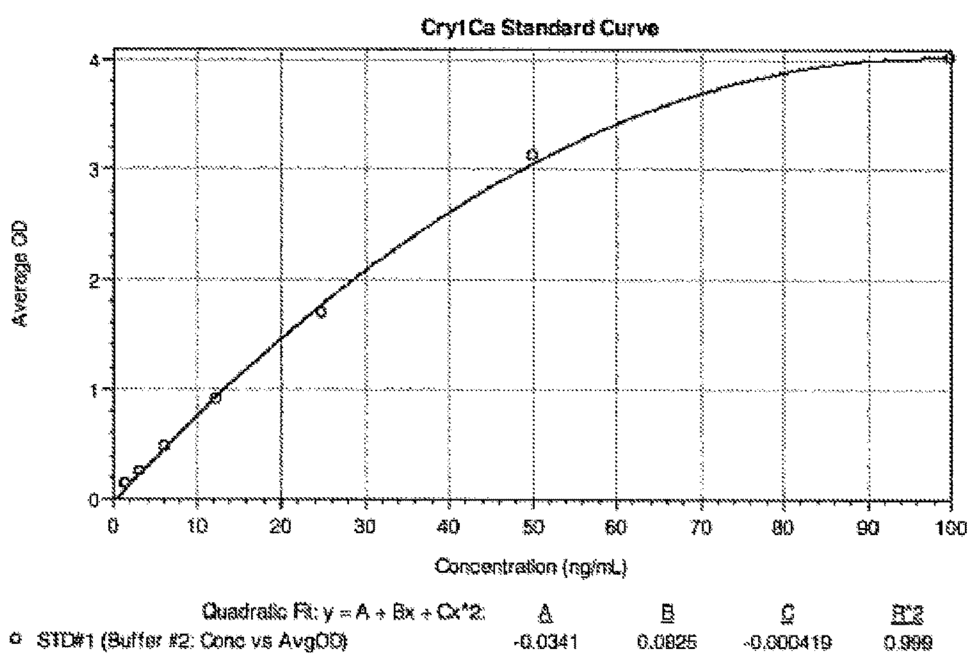
FIG. 1 is a Cry1Ca standard curve. Seven concentrations of the reference Cry1Ca protein were tested and were shown to have linearity using the quadratic curve fitting analysis. Acceptable correlation was shown by an $r^2$ value of 0.999.

The present invention encompasses the mAbs listed in Table 1, and the hybridomas that produce the mAb, that specifically bind with Cry1Ca core toxin.

TABLE 1

| Hybridoma/mAb Designation | ATCC Deposit Designation | ATCC Deposit Date |
|---|---|---|
| 3-34 | PTA-121061 | 5 Mar. 2014 |
| 4-39 | PTA-121062 | 5 Mar. 2014 |
| 4-45 | PTA-121063 | 5 Mar. 2014 |
| 4-40 | PTA-121064 | 5 Mar. 2014 |
| 4-41 | PTA-121065 | 5 Mar. 2014 |
| 4-42 | PTA-121066 | 5 Mar. 2014 |

These mAbs are surprisingly well suited for detecting both Cry1Ca holotoxin and Cry1Ca core toxin expressed by transgenic events in a variety of plants and plant tissues. The invention further provides quantitative and qualitative immunoassays using the immunoglobulins of the invention. A two-mAb sandwich ELISA was validated for the determination of Cry1Ca protein in corn leaf tissue. The full-length Cry1Ca reference standard curve from 1.525-100 ng/mL was determined to have linearity based on the quadratic fit analysis and a correlation of 0.999. The Cry1Ca ELISA is accurate when comparing samples for similar protein levels by two analytical methods (ELISA and western blot analysis) as well as recovery of Cry1Ca protein when compared to the theoretical concentration of the protein spiked into corn matrix. This assay also precisely determined protein levels over multiple assay days. When testing corn samples, measurements of protein levels were parallel over five dilutions, so unbiased measurements will not occur based on the dilution needed for corn samples.

The invention also includes a method of using the claimed antibodies for identifying the presence of Cry1Ca in a biological sample comprising: a) immobilizing said antibody onto an assay surface; b) contacting said assay surface with a liquid suspected of containing Cry1Ca and washing said assay surface with a suitable solution; c) contacting said assay surface with an anti-Cry1Ca antibody labeled with a reporting group and washing said assay surface with a suitable solution; d) detecting the presence of said reporting group.

The invention further includes an analytical method for the quantitative determination of Cry1Ca toxin expressed in transgenic plants, especially soybean and cotton plants. The Cry1Ca protein is extracted from soybean samples with a PBST (phosphate buffered saline solution containing 0.05% Tween™ 20) solution. The extract is centrifuged; the aqueous supernatant is collected and diluted. An aliquot of the diluted sample is incubated with enzyme-conjugated anti-Cry1Ca monoclonal antibody in the wells of an anti-Cry1Ca polyclonal or monoclonal antibody-coated plate in a sandwich ELISA format. Both antibodies in the sandwich pair capture the Cry1Ca protein in the sample. At the end of the incubation period, the unbound reagents are removed from the plate by washing with PBST. The presence of Cry1Ca is detected by incubating the enzyme conjugate with an enzyme substrate, generating a colored product. Since the Cry1Ca is bound in the antibody sandwich, the level of color development is proportional to the concentration of Cry1Ca in the sample (i.e., lower protein concentrations result in lower color development). The absorbance at 450 nm minus absorbance at a reference wavelength (such as 650 nm) is measured using a plate reader. A calibration curve is estimated from 7 standard concentrations using a quadratic regression equation. This Cry1Ca ELISA is specific and sensitive enough for the quantitation of Cry1Ca in plant tissue sample extracts. In addition the antibodies of the invention may be used to confirm the presence of Cry1Ca using a standard western blotting procedure.

The preparation of antibodies against proteins of interest is well known in the art. See Galfre and Milstein, Methods in Enzymology, Vol. 73, Academic Press, New York (1981); James W. Goding, Monoclonal Antibodies: Principles and Practice, Academic Press, Orlando, Fla. (1986); Current Protocols in Molecular Biolopy, F. M. Ausubel, et al. ed., Wiley Interscience, New York, (1987).

To prepare antibodies reactive with a protein of interest, the protein must be first enriched or purified. Relatively crude antigenic preparations of the protein may be used for immunization purposes. However, highly purified protein is required to determine accurately if hybridomas are producing the sought after monoclonal antibodies or to assay the antibody titers of immune serum.

Once the Cry1Ca has been isolated, antibodies specific for Cry1Ca may be raised by conventional methods that are well known in the art. Repeated injections into a host of choice over a period of weeks or months will elicit an immune response and result in significant anti-Cry1Ca serum titers. Preferred hosts are mammalian species and more highly preferred species are rabbits, goats, sheep and mice. Blood drawn from such immunized animals may be processed by established methods to obtain antiserum (polyclonal antibodies) reactive with Cry1Ca. The antiserum may then be affinity purified by adsorption to Cry1Ca according to techniques known in the art. Affinity purified antiserum may be further purified by isolating the immunoglobulin fraction within the antiserum using procedures known in the art. The resulting material will be a heterogeneous population of immunoglobulins reactive with Cry1Ca.

Anti-Cry1Ca mAbs are readily prepared using purified Cry1Ca. Methods for producing mAbs have been practiced for several decades and are well known to those of ordinary skill in the art. Repeated intraperitoneal or subcutaneous injections of Cry1Ca in adjuvant will elicit an immune response in most animals, especially mice. Hyperimmunized B-lymphocytes are removed from the animal and fused with a suitable fusion partner cell line capable of being cultured indefinitely. Numerous mammalian cell lines are suitable fusion partners for the production of hybridomas. Many such lines are commercially available from the ATCC and commercial suppliers.

Once fused, the resulting hybridomas are cultured in a selective growth medium for one to two weeks. Two well known selection systems are available for eliminating unfused myeloma cells or fusions between myeloma cells from the mixed hybridoma culture. The choice of selection system depends on the strain of mouse immunized and myeloma fusion partner used. The AAT selection system, described by Taggart and Samloff, Science 219, 1228 (1982), may be used; however, the HAT (hypoxanthine, aminopterin, thymidine) selection system, described by Littlefield, Science 145, 709 (1964), is preferred because of its compatibility with mouse cells and fusion partners mentioned above.

Spent growth medium is then screened for immunospecific mAb secretion. Enzyme linked immunosorbant assay procedures are best suited for this purpose; though, radioimmune assays adapted for large volume screening are also acceptable. Multiple screens designed to consecutively pare down the considerable number of irrelevant or less desired cultures must be performed to isolate the small percentage of mAbs of the instant invention. Cultures that secrete mAbs reactive with Cry1Ca were isotyped using commercially available assays.

Hybridoma cultures which secrete the sought-after anti Cry1Ca mAbs should be sub-cloned several times to establish monoclonality and stability. Well known methods for sub-cloning eukaryotic, non-adherent cell cultures include limiting dilution, soft agarose and fluorescence activated cell sorting techniques. After each subcloning, the resultant cultures must be re-assayed for antibody secretion and isotype to ensure that a stable antibody-secreting culture has been established.

The claimed anti-Cry1Ca antibodies can be immobilized to a surface so that some of the antibody binding site remains exposed and capable of binding Cry1Ca. A wide assortment of schemes for immobilizing antibodies has developed over the past few decades. Immobilization can be accomplished by covalently coupling the antibody directly to the desired surface or by bridging the antibody to the surface.

CNBr and carbodiimide coupling of antibodies to polysaccharide based beads such as Sepharose® (Pharmacia, Piscataway, N.J.) are illustrative of direct coupling schemes that are consistent with the invention. Direct couplings generally do not orient the antibodies in any particular fashion; however, some types of direct couplings are able to reproducibly orient the antibody on the immobilizing substance.

Preferred coupling schemes orient the antibody such that its antigen binding regions remain exposed. One such scheme utilizes the natural carbohydrate found on the heavy chains of the antibody. By first oxidizing the carbohydrate moieties to the corresponding aldehydes then reacting the aldehyde with a primary amino group on the surface, it is possible to link the antibody in an advantageous orientation.

Many types of bridges are possible and include small organic linkers which covalently bind the antibody to the immobilizing substance. Such spacer arms are acceptable and preferably should not interact with proteins once the bridge has been formed.

The above discussion is in no way meant to limit the scope of the invention. Numerous other well known schemes for linking antibodies to immobilizing substances are consistent with the invention.

It is well known that antibodies labeled with a reporting group can be used to identify the presence of antigens in a variety of milieus. Antibodies labeled with radioisotopes have been used for decades in radioimmune assays to identify, with great precision and sensitivity, the presence of antigens in a variety of biological fluids. More recently, enzyme labeled antibodies have been used as a substitute for radio-labeled antibodies in the popular ELISA.

Antibodies of the present invention can be bound to an immobilizing substance such as a polystyrene well or particle and used in immunoassays to determine whether Cry1Ca is present in a test sample. In this embodiment of the invention, a sample is contacted with the immunoaffinity surface and allowed to incubate. After a washing step, any Cry1Ca that has bound to the immunoaffinity surface is detected by contacting the surface with another antibody of the invention labeled with a reporting group.

The use of lateral flow strips or immunochromatographic strips with the claimed antibodies and assay methods is consistent with the invention. Lateral flow assays are well known in the art. See for example U.S. Pat. No. 6,485,982. In this mode lateral flow tests can be used for qualitative or semi-quantitative detection of Cry1Ca alone or simultaneously with other analytes. Lateral flow tests are the simplest to use of all the test formats described herein and are particularly useful in field settings where plant material is quickly extracted into a solution and tested on a lateral flow strip. In this mode it is only necessary to place the lateral flow strip into a liquid sample or to apply the liquid sample to the lateral flow strip and read the results after a predetermined time. All lateral flow tests should incorporate either a procedural control line or a sample control line that is used to validate the test result. Appearance of two lines, therefore, indicates a positive result, while a valid negative test produces only the control line. If only the test line appears, or if no lines appear, it is invalid.

A typical lateral flow test strip consists of four main components; a sample pad upon which the test sample is applied, a conjugate pad that contains antibodies of the present invention conjugated to colored particles (typically colloidal gold particles, or latex microspheres); a reaction membrane such as a hydrophobic nitrocellulose or cellulose acetate membrane onto which a different antibody of the invention is immobilised in a line across the membrane as a capture zone or test line; and, a waste reservoir designed to draw the sample across the reaction membrane by capillary action.

The components of the lateral flow strip are normally fixed to an inert backing material and may be presented in a simple dipstick format or within a plastic casing with a sample port and reaction window showing the capture and control zones. In another mode of the assay embodiment, a test sample suspected of containing Cry1Ca is dried onto a surface, forming an immobilized test sample. A labeled antibody of the invention is then contacted with the immobilized test sample and allowed to incubate. If the sample contains Cry1Ca, the labeled antibody will bind to the immobilized Cry1Ca. This method can also be done using an unlabeled antibody of the invention followed by a labeled secondary antibody that binds to an antibody of the invention which has already bound to Cry1Ca. After washing, the immobilized test sample is measured to detect the presence of any reporting groups.

Reporting groups are typically enzymes such as alkaline phosphatase, horseradish peroxidase or beta-D-galactosidase. Suitable substrates produce a color change when reacted with the enzyme. In so doing, measurements of the color intensity can be quantitated using a spectrophotometer. If the reporting group is a radioisotope, an appropriate gamma or beta ray detecting instrument can be used to quantitate the reporting group. The intensity of the reporting group directly correlates, with the amount of Cry1Ca in the test sample.

The following examples will help describe how the invention is practiced and will illustrate the characteristics of the claimed anti-Cry1Ca antibodies and assays.

EXAMPLE 1

Immunogen Preparation

Full length Cry1Ca holotoxin was produced using a *Pseudomonas fluorescens* protein expression system. See for example Retallack et al., *Protein Expression and Purification*; Vol 81, 2, pp 157-165; February 2012. Five to Ten grams cell paste was used to prepare protein samples. For high expressers (up to 0.5 g/l), 5 g of cell paste was sufficient. For low expressers, typically 10 g of cell paste was processed. The host cells were suspended in 10-20 volumes or 100 ml solution containing 20 mM Tris-HCl, pH 8, 150 mM NaCl, 5% Glycerol, 5 mM EDTA, 1 mM DTT with a homogenizer (Pro Scientific Inc., Model Pro300A) and sonicated on ice for 10 min (Branson Sonifier Model 450). Supernatant containing soluble proteins was discarded after 20 min centrifugation at 12 k rpm. The pellet containing target proteins was washed in 100 ml fresh solution (as before), and then centrifuged. This process was repeated 2-3 times until the recovered inclusion body (IB) was clear. 10 ml of 50 mM CAPS, pH 11 solution containing 10 mM DTT and 4 M Urea was added per gram of IB (wet weight), and the protein was solubilized at room temperature for approximately 2 hours on a rocking plate. The sample was centrifuged at 12 krpm for 20 min and the supernatant was transferred into a SnakeSkin™ pleated dialyze tubing (Thermo Scientific, 10 kDa cut-off) and dialyze against 1 L of 50 mM CAPS, pH 11 with 10 mM DTT at 4° C. overnight. The sample was centrifuged at 12 k rpm for 20 minutes to remove any precipitation.

The supernatant was collected and applied onto a 5 ml HiTrap™ Q (GEHC, Fast Flow or High Performance column) at 5 ml/min. The column was washed for 2-3 column volume, then eluted using 0-100% buffer B (1 M NaCl in buffer A, equal to 50 mM CAPS, pH 11, 10 mM DTT) over 20 minutes while 2.5 ml fractions were collected. Peak elutes were then analyzed by SDS-PAGE. Cry1Ca eluted from 20-45 mS/cm of salt, corresponding to fraction number 10-20, and 20 μl of sample was withdrawn for gel analysis. The majority of earlier eluted peaks containing Cry1Ca core protein were pooled, and transferred into a Millipore concentration unit with 50 KDa cut-off filter, and centrifuged at 4000 rpm at room temperature for 5-15 minutes that resulted in a final sample volume of approximately 1 ml. The sample was injected onto a 24 ml Superdex™ 200 column (10/300 dimension) at 1 ml/min. The size column was run with 20 mM CAPS, pH 11, 0.1 M NaCl, and 10 mM DTT buffer, and 1 ml fractions were collected. 20 μl of sample aliquot was analyzed on SDS-PAGE for the fractions covering the major peaks. Typically higher oligomer eluted at 13-14 minutes, and smaller monomeric target protein eluted at or after 16 minutes. The purified Cry1Ca toxin was pooled, and stored at −20° C.

Amino truncated Cry1Ca core toxin (residues 29-628) was prepared for further assay validation studies by trypsin cleavage of the holotoxin. A sample of purified Cry1Ca holotoxin showed a positive signal of the expected size by western blot using anti-Cry1Ca polyclonal antibody. Bioactivity of the purified Cry1Ca holotoxin and amino truncated core toxin was confirmed by an insect bioassay using neonate Diamondback moth larvae fed on Cry1Ca spiked diet.

EXAMPLE 2

Hybridoma Preparation

Mice were immunized with purified Cry1Ca, and standard hybridoma fusion techniques were used to prepare a panel of hydridomas expressing anti Cry1Ca monoclonal antibodies. Samples of spent tissue culture media were removed aseptically from each well containing a hybridoma culture and assayed for Cry1Ca reactivity using the following antibody capture ELISA method. Microtiter wells were coated with a solution of 1-10 μg/mL of purified Cry1Ca. The wells were washed and samples of spent tissue media were placed in the wells and allowed to incubate. The wells were washed and horseradish peroxidase-labeled goat anti mouse antiserum was added and allowed to incubate. The plates were washed, substrate was added to develop a color reaction and the plates were read for OD (optical density). Wells with high OD readings were mapped back to culture wells containing the hybridomas. The Cry1Ca antibody positive cultures were continually screened for antibody production to assure growth stability and antibody production as the cultures were expanded. Several rounds of limiting dilution cloning were performed to establish true monoclonality for each culture. Further assays on antibody positive clones were conducted to determine the suitability of each antibody for use in the presently claimed detection methods for field use with plant material. The monoclonal antibodies were screened for specificity to Cry1Ca holo and core toxin. All the antibodies were tested for cross-reactivity and none were found to cross react with Cry1Ab, Cry1Ac, Cry1Be, Cry1Da, and Cry1F.

EXAMPLE 3

Quantitative ELISA Validation Study

Antibody 4-40 was used as the capture antibody and was coated on a 96 well microtiter plate at a concentration of 1 ug/ml in PBST (phosphate buffered saline solution containing 0.05% Tween™ 20) with 0.75% ovalbumin (PBST/OVA) then stored under refrigeration. The detection antibody, 4-42, was conjugated to horseradish peroxidase (HRP) using standard techniques. An assay kit consisting of an antibody coated microtiter plate, liquid HRP conjugate of 4-42 (1×), enzyme substrate solution, and standard reaction stopping agent was prepared to use in this validation experiment.

Linearity testing consisted of testing the Cry1Ca kit with a Cry1Ca holotoxin protein standard curve diluted in buffer to determine if the curve was linear across all concentrations. A coated anti-Cry1Ca assay plate was brought to room temperature (about 30 minutes). A Cry1Ca protein standard (100 ng/mL in PBST) was prepared. PBST was used as the dilution buffer for this experiment unless otherwise noted.

200 uL of the Cry1Ca standard was added in triplicate to Row A, Columns 10-12. 100 uL of PBST buffer was added to remaining wells in Columns 10-12. A 2-fold serial dilution was performed down the columns of the plate by taking 100 μL of the first standard and adding to the next well containing buffer that produced a Cry1Ca standard curve of 100, 50, 25, 12.5, 6.25, 3.125, and 1.4525 ng/mL. The plate was sealed and shaken at room temperature for 1 hour using a plate shaker. The plate was washed four times with PBST using a QuadraWash™ 2 plate washer, (Tomtec).

After washing, 100 μL of Cry1Ca/HRP enzyme conjugate was added to the wells of the plate. The plate was sealed and shaken at room temperature for 30 minutes. The plate was then washed using the plate washer. 100 μL of HRP substrate solution was added to the wells of the plate and incubated for 15 minutes at room temperature. 100 μL of stop solution (0.4 M $H_2SO_4$) was added to the wells of the plate. The plate was then read at 450 nm with a SpectraMax™ plate reader (Molecular Devices).

The reference Cry1Ca standard curve (100, 50, 25, 12.5, 6.25, 3.125, and 1.4525 ng/mL) showed that these concentrations were linear based on quadratic fit analysis (FIG. 1). This linearity was determined based on the correlation ($r^2$) value being 0.999. This curve was used for all subsequent testing by ELISA for this validation.

Figure 2:
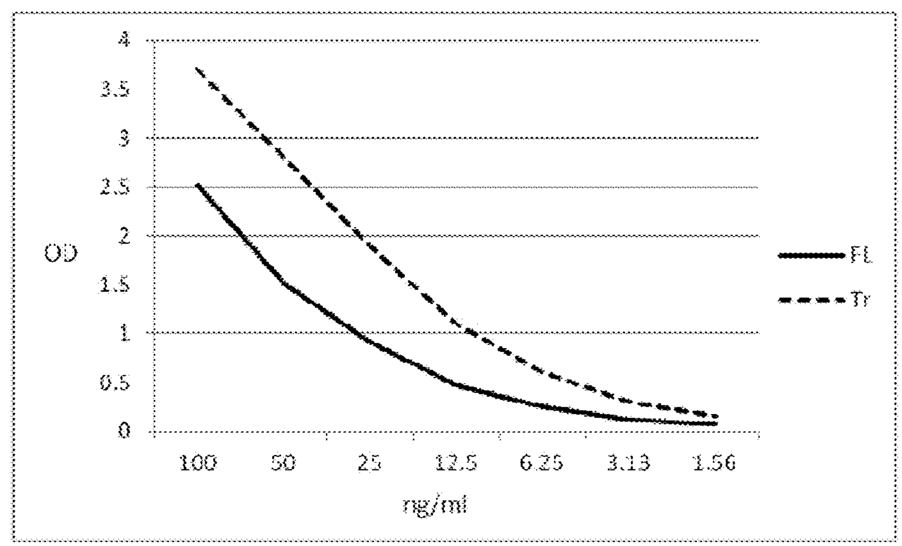
FIG. 2 is a comparison of amino truncated and full length Cry1Ca ELISA standard curves showing the slope difference between the two standards.

The assay above was repeated using truncated Cry1Ca core toxin and was compared to the holotoxin results (FIG. 2). Due to the size difference of approximately 100% between holo and core toxins, the slope of the full length toxin was markedly different than the slope of the core toxin. This level I validation study demonstrated ELISA assays for detecting either Cry1Ca holo or core toxin with defined levels of performance needed to provide a high degree of confidence in the results produced.

The precision of these methods were determined using the results of standard 'spike-in' experiments over multiple days. The standards were distributed into single-use vials and stored at −80° C. until used for testing. The standard deviations and percent coefficient of variation were calculated for each of six total spike-in replicates. The coefficient of variation was calculated for each level of fortification with an acceptable range of <20% between the expected concentrations of 50-0.80 ng/ml as shown in Table 2.

TABLE 2

| Values in ng/ml Expected concentration | Rep 1 | Rep 2 | Rep 3 | Rep 4 | Rep 5 | Rep 6 | Precision % CV |
|---|---|---|---|---|---|---|---|
| 200 | 150 | 280 | 180 | 160 | 200 | 120 | 30% |
| 100 | 98 | 110 | 171 | 88 | 110 | 93 | 27% |
| 50 | 64 | 58 | 58 | 45 | 54 | 50 | 12% |
| 25 | 27 | 30 | 29 | 25 | 25 | 22 | 11% |
| 13 | 13 | 14 | 13 | 12 | 11 | 11 | 10% |
| 6.3 | 7.3 | 7.5 | 6.8 | 6.1 | 6.1 | 5.5 | 12% |
| 3.1 | 3.4 | 4.1 | 3.5 | 3.3 | 3.3 | 3.2 | 9% |
| 1.6 | 2.2 | 2.2 | 1.9 | 1.8 | 1.7 | 1.6 | 13% |
| 0.80 | 1.2 | 1.1 | 0.93 | 0.89 | 0.88 | 0.81 | 15% |
| 0.40 | 0.52 | 0.43 | 0.28 | 0.32 | 0.33 | 0.35 | 24% |
| 0.20 | 0 | 0 | 0 | 0 | 0 | 0.05 | 245% |

EXAMPLE 4

Selectivity/Matrix Effect

Null transgenic corn leaf tissue was tested for matrix interference with the Cry1Ca standard. A mixture of corn leaf tissue was placed into 50 mL conical tubes with 40 mL of Extraction Buffer (PBST+5 ul/ml of Plant Protease Inhibitors Cat # P9599 Sigma) and 40 Daisy™ BBs (4.5 mm). The tubes were shaken for 3 minutes in a modified paint shaker then centrifuged for 10 minutes at 3600 rpm. The supernatant was removed, placed on ice and tested for total soluble protein using the Pierce BCA Protein Assay Kit (Cat # 23227, Thermo Scientific). Once the total protein concentration was determined, the matrix was diluted to 0.24 mg/mL in PBST as used as the corn matrix.

Purified Cry1Ca protein standard was diluted to 100 ng/mL in corn matrix solution and 100 μL was added to the wells of a Cry1Ca coated microtiter assay plate in triplicate in Row A, Column 10-12. 100 μL of corn matrix (without Cry1Ca standard) was added to the remaining wells of the plate. A 2-fold serial dilution was performed down the columns of the assay plate and was tested using the ELISA kit from Example 3. The matrix effect was determined by the % recovery determined by the ELISA for each standard concentration compared to the theoretical protein amount added to the matrix. The reference Cry1Ca spiked into the corn matrix was used to determine if Cry1Ca could be detected at acceptable levels when in the presence of corn matrix. A corn sample would normally be diluted 1:25, therefore the total extractable soluble protein concentration in the sample is 0.24 mg/mL. This concentration will be used for all tests with corn matrix.

Based on the ELISA results, each of the seven Cry1Ca standard concentrations had acceptable signal (80-120%) as compared to the theoretical protein spiked into the matrix (Table 3). Thus, there was no matrix effect observed in any of the Cry1Ca standards with the corn matrix concentration tested.

TABLE 3

| Theoretical Cry1Ca Conc. (ng/mL) | Actual Cry1Ca Conc. in Corn Matrix (ng/mL) | % Recovery of Cry1Ca |
|---|---|---|
| 100 | 115 | 115 |
| 50 | 48 | 96 |
| 25 | 23.5 | 94 |
| 12.5 | 12.6 | 101 |
| 6.25 | 6.9 | 110 |
| 3.125 | 3.3 | 106 |
| 1.5625 | 1.6 | 102 |

EXAMPLE 5

Accuracy

The accuracy of the assay was determined by comparing ELISA results with a western blot. Three leaf samples from corn plants genetically engineered to express Cry1Ca holo-toxin were extracted as described above. The samples were then centrifuged for 5 minutes at 3600 rpm. 100 μL of supernatant was removed and placed on ice until use in ELISA. 200 μL of extraction buffer was added to the samples, and the extraction process was repeated. The supernatants from both extractions were then pooled together. The samples were diluted at 2, 4, 8, 16, and 32 dilutions in duplicate and added to an ELISA plate. Cry1Ca standard was prepared and added to the plate in duplicate starting at 100 ng/mL. The ELISA assay was then run based on the methods above. All dilutions for each sample were averaged together to get the average ng/mL value for each corn sample.

Three corn samples were tested by western blot analysis in duplicate using the extracts from the ELISA testing above. After the supernatant was collected, 4×loading buffer (NU-PAGE LDS Sample Buffer, Invitrogen) containing 400 mM dithiothreitol (DTT) was added to the sample extract to make the final concentration 1×. The samples were heated for 5 minutes at 90° C. The samples, full-length Cry1Ca protein standard (20 ng/lane, 10 ng/lane), truncated Cry1Ca protein standard (20 ng/lane, 10 ng/lane), and negative corn matrix were loaded into a 4-12% Bis-Tris NUPAGE Mini Gel (Invitrogen). Once each lane of the gel was loaded, the gel box was run at 200V for 45 minutes. After gel separation, the proteins were transferred to a membrane by tank transfer. The blot module (Xcell II Blot™ module, Invitrogen) was assembled in the following order: bottom (negative electrode) part of the module, 3 pre-wet filter pads, 1 pre-wet filter paper, mini gel, membrane (PVDF, Invitrogen), 1 pre-wet filter paper, 3 pre-wet filter pads, and the top (positive electrode) part of the module. The transfer sandwich was then placed in the transfer tank, and 1×Transfer Buffer (Invitrogen) was added to the inner and outer chambers of the tank. The gel was transferred at 5V overnight in the cold room. After transfer, the membrane was blocked with ECL Blocking Agent (Amersham Biosciences) for 60 minutes at room temperature while shaking at 50 rpm. The blocking solution was removed, and the primary antibody (rabbit anti-Cry1Ca truncated), diluted to 1 ug/mL in blocking buffer, was added to the membrane for 1 hour at room temperature with shaking. The primary antibody was removed, and the blot was rinsed two times with PBST and washed two times for 5 minutes with PBST. After washing, the secondary antibody (goat anti-rabbit HRP, KPL), diluted 1:5000 with PBST, was added to the membrane and incubated for 1 hour at room temperature while shaking. The secondary antibody was then removed and the membrane was rinsed 3 times with PBST, washed 4 times for 5 minutes each with PBST, and then rinsed 3 times with 1×PBS. After washing, the blot was subjected to 4 mL of chemiluminescent substrate (Pierce SuperSignal West Pico Luminol Enhancer™ and Stable Peroxide Solution) for 4 minutes. The substrate was removed, and the blot was wrapped in plastic wrap. The blot was then taken into a dark room and exposed to film to detect the proteins present on the gel. Once the protein image was displayed on the film, the film was scanned on a Syngene XR Imager (Syngene) and densitometry was determined on the standard and sample bands using the Quantity One™ software (Bio-Rad). The results are shown in Table 4.

TABLE 4

| Samples | ELISA (ng/mL) | Western (ng/mL) | % Difference |
|---|---|---|---|
| Plant 1 | 387 | 428 | 10.8 |
| Plant 2 | 431 | 338 | 21.5 |
| Plant 3 | 462 | 531 | 14.9 |

EXAMPLE 6

Parallelism

The Cry1Ca assay was tested for parallelism to ensure the claimed antibodies supported an assay in which multiple serial dilutions of samples would not result in a biased measurement of Cry1Ca-expressing corn plants. Six leaf samples of corn genetically modified to express Cry1Ca were tested by ELISA. It was found that for each sample, five dilutions (1:4, 1:8, 1:16, 1:32, and 1:64) fell within the quantitative range of the standard curve, and the CV (coefficient of variation) of the quantified results was less than 20% as shown in Table 5. Each sample was tested in triplicate, and an average concentration was determined for each dilution within the individually tested sample. SD corresponds to standard deviation, which is used to determine % CV. There was no trend of increasing or decreasing estimates of the protein concentration over the dilution range tested. Thus, the Cry1Ca ELISA demonstrated parallelism across five dilutions for Cry1Ca-positive corn plants.

TABLE 5

| Dilution | Sample 1 | Sample 2 | Sample 3 | Sample 4 | Sample 5 | Sample 6 |
|---|---|---|---|---|---|---|
| 1:4 | 508.191 | 508.191 | 508.191 | 508.191 | 508.191 | 508.191 |
| 1:8 | 470.131 | 628.031 | 323.393 | 394.814 | 440.835 | 622.827 |
| 1:16 | 438.126 | 477.366 | 331.533 | 396.013 | 412.269 | 495.308 |
| 1:32 | 481.099 | 512.159 | 369.047 | 407.615 | 450.533 | 532.541 |
| 1:64 | 526.427 | 532.907 | 401.336 | 449.713 | 498.186 | 578.982 |
| Average | 484.7948 | 531.7308 | 386.7 | 431.2692 | 462.0028 | 547.5698 |
| SD | 34.23188 | 57.37556 | 74.72797 | 48.4475 | 40.29782 | 52.81624 |
| CV | 7.061106 | 10.79034 | 19.32453 | 11.2337 | 8.722419 | 9.645573 |

What is claimed is:

1. A monoclonal antibody that specifically binds to Cry1Ca core toxin, said monoclonal antibody selected from the group consisting of monoclonal antibodies produced by the hybridomas having American Type Culture Collection (ATCC) accession numbers PTA-1210161, PTA-121062, PTA-121063, PTA-121064, PTA-121065, and PTA-121066.

2. The monoclonal antibody of claim 1, wherein the monoclonal antibody is produced by the hybridoma having ATCC accession number PTA-121061.

3. The monoclonal antibody of claim 1, wherein the monoclonal antibody is produced by the hybridoma having ATCC accession number PTA-121062.

4. The monoclonal antibody of claim 1, wherein the monoclonal antibody is produced by the hybridoma having ATCC accession number PTA-121064.

5. The monoclonal antibody of claim 1, wherein the monoclonal antibody is produced by the hybridoma having ATCC accession number PTA-121065.

6. The monoclonal antibody of claim 1, wherein the monoclonal antibody is produced by the hybridoma having ATCC accession number PTA-121066.

7. The monoclonal antibody of claim 1, wherein the monoclonal antibody is produced by the hybridoma having ATCC accession number PTA-121063.

8. A hybridoma cell line that produces a monoclonal antibody of claim 1 that is on deposit with the American Type Culture Collection (ATCC), wherein the hybridoma cell line is deposited under the accession number selected from the group consisting of PTA-121061, PTA-121062, PTA-121063, PTA-121064, PTA-121065, and PTA-121066.

9. The hybridoma cell line of claim 8, wherein the hybridoma cell line is deposited under ATCC accession number PTA-121061.

10. The hybridoma cell line of claim 8, wherein the hybridoma cell line is deposited under ATCC accession number PTA-121062.

11. The hybridoma cell line of claim 8, wherein the hybridoma cell line is deposited under ATCC accession number PTA-121063.

12. The hybridoma cell line of claim 8, wherein the hybridoma cell line is deposited under ATCC accession number PTA-121064.

13. The hybridoma cell line of claim 8, wherein the hybridoma cell line is deposited under ATCC accession number PTA-121065.

14. The hybridoma cell line of claim 8, wherein the hybridoma cell line is deposited under ATCC accession number PTA-121066.

15. A method for identifying the presence of Cry1Ca core toxin in a sample comprising:

a) immobilizing a first monoclonal antibody onto an assay surface then washing said assay surface, wherein the first monoclonal antibody is selected from the group consisting of monoclonal antibodies produced by the hybridomas having American Type Culture Collection (ATCC) accession numbers PTA-1210161, PTA-121062, PTA-121-063, PTA-121064, PTA-121065, and PTA-121066;

b) contacting the assay surface having the immobilized first monoclonal antibody with the sample suspected of containing Cry1Ca core toxin for a period of time sufficient to allow binding to Cry1Ca core toxin then washing the assay surface;

c) contacting the assay surface having the immobilized first monoclonal antibody bound to Cry1Ca core toxin with a second monoclonal antibody conjugated to a reporting group for a period of time sufficient to allow binding of the second conjugated monoclonal antibody to Cry1Ca core toxin then washing said assay surface, wherein the second monoclonal antibody is selected from the group consisting of monoclonal antibodies produced by the hybridomas having American Type Culture Collection (ATCC) accession numbers PTA-1210161, PTA-121062, PTA-121-063, PTA-121064, PTA-121065, and PTA-121066, and wherein the second monoclonal antibody is a different monoclonal antibody than the first monoclonal antibody; and d) detecting the presence or absence of said reporting group, thereby detecting the presence or absence of Cry1Ca core toxin.

16. A method for the quantitative determination of Cry1Ca core toxin in a sample comprising:

a) immobilizing a first anti-Cry1Ca core toxin antibody onto an assay surface;

b) contacting the assay surface having the immobilized first anti-Cry1Ca core toxin antibody with the sample suspected of containing Cry1Ca core toxin for a period of time sufficient to allow binding to Cry1Ca core toxin then washing the assay surface;

c) contacting the assay surface having the immobilized first anti-Cry1Ca core toxin bound to Cry 1Ca core toxin with a second antibody conjugated to a reporting group for a period of time sufficient to allow binding of said second antibody to Cry1Ca core toxin then washing the assay surface, wherein the second antibody is a monoclonal antibody selected from the group consisting of monoclonal antibodies produced by the hybridomas having American Type Culture Collection (ATCC) accession numbers PTA-1210161, PTA-121062, PTA-121-063, PTA-121064, PTA-121065, and PTA-121066, and wherein the second antibody is a different antibody than the first anti-Cry1Ca core toxin antibody; and d) determining the intensity of the reporting group and comparing the determined intensity to a calibration curve, thereby determining the quantity of Cry1Ca core toxin in the sample.

17. The method of claim 15 wherein the first monoclonal antibody is the monoclonal antibody produced by the hybridoma having ATCC accession number PTA-121064 and the second monoclonal antibody is the monoclonal antibody produced by the hybridoma having ATCC accession number PTA-121066.

* * * * *